(12) United States Patent
Boeck

(10) Patent No.: US 7,942,146 B2
(45) Date of Patent: May 17, 2011

(54) IMPACTION NOZZLE FOR PROPELLANT DRIVEN METERED DOSE AEROSOLS

(75) Inventor: Georg Boeck, Laupheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 931 days.

(21) Appl. No.: 11/072,375

(22) Filed: Mar. 4, 2005

(65) Prior Publication Data

US 2008/0041387 A1    Feb. 21, 2008

(30) Foreign Application Priority Data

Mar. 5, 2004  (DE) .................. 10 2004 011 381

(51) Int. Cl.
*A61M 11/00*   (2006.01)
*B05B 7/32*    (2006.01)
*F23D 11/24*   (2006.01)
*F23D 14/28*   (2006.01)
*F23D 14/34*   (2006.01)

(52) U.S. Cl. .................. 128/200.23; 239/337
(58) Field of Classification Search ........... 128/200.14, 128/200.18, 200.21, 200.23, 200.24, 203.15, 128/205.24; 222/330, 635; 239/337, 426, 239/433, 434, 543, 544
See application file for complete search history.

(56) References Cited

U.S. PATENT DOCUMENTS

| 3,236,418 | A | * | 2/1966 | Dalle et al. ............... 222/135 |
| 3,236,457 | A | * | 2/1966 | Ladd et al. ............... 239/304 |
| 3,367,330 | A |   | 2/1968 | Sierpin |
| 3,383,879 | A | * | 5/1968 | Tice ....................... 62/293 |
| 3,730,437 | A | * | 5/1973 | Rousselot ................ 239/306 |
| 3,920,158 | A | * | 11/1975 | Meshberg ................ 222/135 |
| 4,103,684 | A | * | 8/1978 | Ismach .................... 604/71 |
| 4,217,360 | A | * | 8/1980 | Vorbrueggen et al. ...... 514/451 |
| 4,466,838 | A | * | 8/1984 | Heeb et al. ................ 106/311 |

(Continued)

FOREIGN PATENT DOCUMENTS

EP    0261649 A2    3/1988

(Continued)

OTHER PUBLICATIONS

International Search Report for PCT/EP2005/001803 mailed May 25, 2005.

*Primary Examiner* — Kristen C Matter
(74) *Attorney, Agent, or Firm* — Michael P. Morris; David L. Kershner

(57) ABSTRACT

Propellant gas inhaler fitted with a valve or valve system through which at least two clouds of aerosols or at least two jet streams are produced that travel towards one another at an angle from 0° to 180°, so that the individual aerosol particles at least partially impact with one another and lose kinetic energy thereby.

9 Claims, 5 Drawing Sheets

U.S. PATENT DOCUMENTS

| | | | |
|---|---|---|---|
| 4,487,334 A * | 12/1984 | Werding | 222/55 |
| 4,681,258 A * | 7/1987 | Jenkins et al. | 239/66 |
| 4,801,465 A * | 1/1989 | Sponer | 426/116 |
| 5,054,477 A | 10/1991 | Terada et al. | |
| 5,190,029 A | 3/1993 | Byron et al. | |
| 5,249,747 A * | 10/1993 | Hanson et al. | 239/373 |
| 5,301,841 A * | 4/1994 | Fuchs | 222/135 |
| 5,358,179 A * | 10/1994 | Lund et al. | 239/333 |
| 5,472,143 A * | 12/1995 | Bartels et al. | 239/462 |
| 5,524,798 A * | 6/1996 | Stern et al. | 222/402.1 |
| 5,634,571 A * | 6/1997 | Cataneo et al. | 222/80 |
| 5,899,201 A | 5/1999 | Schultz et al. | |
| 6,155,251 A | 12/2000 | Hauser | |
| 6,357,442 B1 | 3/2002 | Casper et al. | |
| 6,737,044 B1 | 5/2004 | Dickinson et al. | |
| 7,195,135 B1 * | 3/2007 | Garcia et al. | 222/137 |
| 2004/0079360 A1 * | 4/2004 | Coffee et al. | 128/200.14 |
| 2004/0184994 A1 | 9/2004 | DeStefano et al. | |
| 2005/0274378 A1 * | 12/2005 | Bonney et al. | 128/200.23 |
| 2006/0239930 A1 | 10/2006 | Lamche et al. | |
| 2007/0221213 A1 | 9/2007 | Wachtel et al. | |

FOREIGN PATENT DOCUMENTS

| | | |
|---|---|---|
| EP | 1003478 A1 | 5/2000 |
| GB | 2324121 A | 10/1998 |
| WO | 9603172 | 2/1996 |
| WO | 0012162 A1 | 3/2000 |
| WO | 02058771 A1 | 8/2002 |
| WO | 2005087298 A1 | 9/2005 |
| WO | 2007110403 A1 | 10/2007 |

* cited by examiner

IMPACTION NOZZLE FOR PROPELLANT DRIVEN METERED DOSE AEROSOLS

RELATED APPLICATIONS

This application claims the benefit under 119(a) of German Patent Application No. 10 2004 011 381 filed on Mar. 5, 2005, which is incorporated herein in its entirety.

BACKGROUND OF THE INVENTION

1. Field of the Invention

The present invention relates to a nozzle or a nozzle system for propellant driven inhalers for the administration of aerosol formulations into the lungs by inhalation.

2. Description of the Prior Art

In propellant driven inhalers, the active substances are stored together with the propellant in cartridge-like canisters. These canisters generally comprise an aluminium container sealed with a valve cup made of aluminium in which a valve is embedded. A canister of this kind can be inserted in the inhaler like a cartridge and is either left there permanently or replaced by a new cartridge after use.

Usually, the canister or container is formed from a casing made of aluminium, aluminium coated on the inside with an inert plastic, or stainless steel and the like. A single container usually has four different zones: the flat or concave inwardly domed base, a cylindrical belly region that merges at its upper third into a tapering neck region, and finally terminating in an edge region, e.g., a crimped edge, that defines the opening of the container.

Typically, these containers are of dimensions such that they can hold a volume of from about 5 to about 50 ml.

In the closed state the container is tightly sealed by the valve cup, usually after being filled or loaded with the pharmaceutical formulation and the propellant. For an example of a valve cup, reference is hereby made to GB 2324121, which is incorporated herein by reference in its entirety.

In the closed state of the canister, the valve cup crimps around the container at its edge at the opening. Generally, a seal seals off the valve cup from the container. The seal may be of annular or disk-shaped construction and consist of materials that are suitable for use in pharmaceutical formulations with fluorohydrocarbons as propellant. Examples include: thermoplastic materials, elastomers, neoprene, isobutylene, isoprene, butyl-rubber, Buna rubber, nitrile rubber, copolymers of ethylene and propylene, terpolymers of ethylene, propylene and a diene, such as butadiene for example, or fluorinate polymers. The preferred materials are ethylene/propylene-diene terpolymers (EPDM). Preferably, the valve cup is substantially planar or substantially defines a plane, which is preferably substantially perpendicular to the longitudinal axis of the canister.

The valve cup is penetrated by a valve that has a valve stem on its side facing the interior of the container and on the outside a nozzle for nebulizing the propellant-containing aerosol formulation. The valve is sealed off from the valve cup in the central opening by a seal. In the simplest case, the valve is cylindrical. The base end of this cylinder projects into the interior of the container, and the head end projects out of the container. The head end contains the nozzle opening. The base end has an inlet for introducing the liquid or gas into the interior of the container.

Valves of this kind have inside them other components, such as springs or valve members. The valve is opened by a vertical movement into the container counter to a spring. A spring counteracts this movement and causes the valve to close automatically after actuation.

When an aerosol formulation is nebulized into an aerosol by means of a propellant driven inhaler known from the prior art by using the adiabatic expansion of the propellant, the aerosol produced travels at high speed. This is due to the fact that the propellant has a high vapor pressure and, consequently, when the valve is opened, a correspondingly high pressure is released. These high speeds mean that a significant part of the aerosol produced is left suspended in the oropharyngeal cavity of the patient inhaling it and is not therefore available to the intended site of activity, the lungs.

SUMMARY OF THE INVENTION

An aim of the invention is to reduce the disadvantages of propellant driven inhalers known from the prior art.

In particular, the invention sets out to modify the valves of propellant driven inhalers so as to produce aerosols traveling at lower speed.

The present invention solves this problem by providing a propellant driven inhaler with a valve or valve system by means of which at least two clouds of aerosol, or at least two spray jets, are produced that travel towards one another at an angle of greater than 0° and equal to or less than 180°, so that the individual aerosol particles at least partially impact with one another and thereby lose kinetic energy. The nozzle openings are preferably arranged so that the linear extensions of the nozzle channels beyond the opening and the longitudinal axis of the nozzle are situated in one plane. In other words, in all the embodiments, the regions of the channels that form the nozzle openings are preferably bent at an angle of greater than 0° and equal to or less than 90° relative to the main longitudinal axis of the valve in question. Angles between 0° and 45° are preferred. An angle of 0° means that the valve opening is aligned with the longitudinal side of the valve.

Accordingly, in a first embodiment, the present invention provides a valve system for a canister that adapted to dispense propellant-driven aerosols. The valve system comprises at least one channel for outwardly conveying a propellant gas formulation loaded in the canister, and two valve openings that are connected to the at least one channel, wherein each valve opening defines a longitudinal axis, and wherein the longitudinal axes intersect to define an angle $\alpha$, wherein $0° < \alpha \leq 180°$, such that jets emerging from the valve openings are directed towards one another, whereby the jets at least partially impact with one another after leaving the valve openings. Preferably, a valve cup is substantially planar or substantially defines a first plane, which is preferably substantially perpendicular to a longitudinal axis of the canister. Because the longitudinal axes of the valve openings intersect to define an angle $\alpha$, wherein $0° < \alpha \leq 180°$, the longitudinal axes of the valve openings can extend along a second plane substantially perpendicular or substantially parallel to the first plane.

Furthermore, in a second embodiment, the present invention provides a bridged valve system for a canister that adapted to dispense propellant-driven aerosols. The bridged valve system comprises a first valve and a second valve fixedly joined together by a bridge, whereby that the two valves can only be moved jointly. Both the first and the second valve comprises at least one channel for outwardly conveying a propellant gas formulation loaded in the canister; and two valve openings that are connected to the at least one channel, wherein each valve opening defines a longitudinal axis, and wherein the longitudinal axes intersect to define an angle $\alpha$, wherein $0° < \alpha \leq 180°$, such that jets emerging from the valve openings are directed towards one another, whereby the jets at least partially impact with one another after leaving the valve openings. Preferably, a valve cup is substantially planar or substantially defines a first plane, which is preferably substantially perpendicular to a longitudinal axis of the canister. Because the longitudinal axes of the valve openings intersect to define an angle $\alpha$, wherein $0°<\alpha\leqq180°$, the longitudinal axes of the valve openings can extend along a second plane substantially perpendicular or substantially parallel to the first plane.

DESCRIPTION OF THE INVENTION

Figure 1:
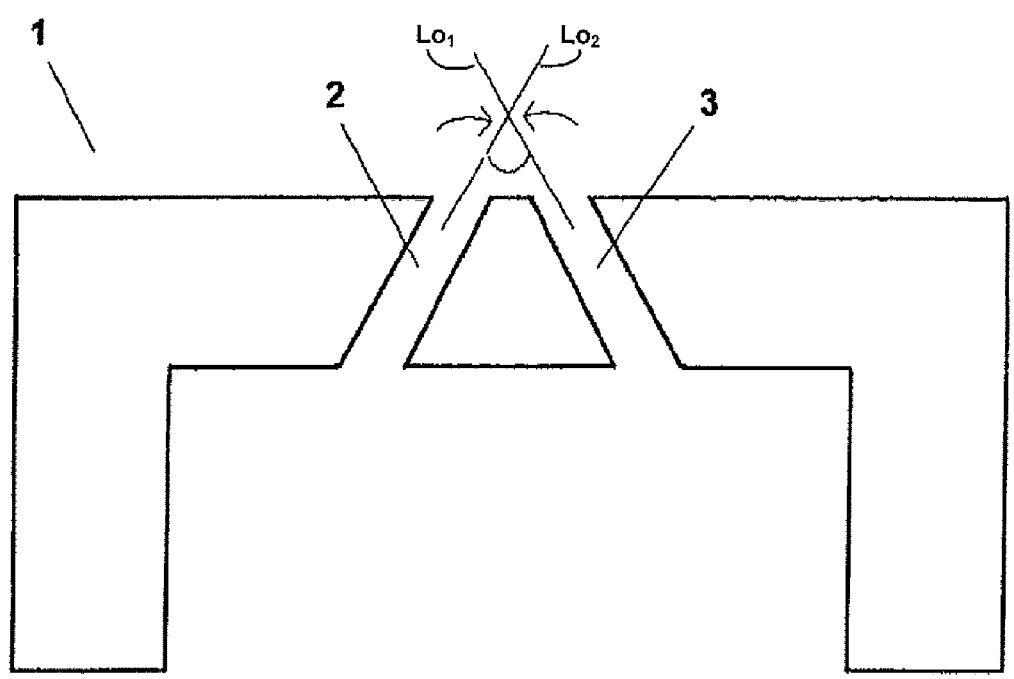
FIG. 1 shows a multi-channel nozzle according to the present invention.

The present invention solves this problem by providing a propellant driven inhaler with a valve or valve system by means of which at least two clouds of aerosol, or at least two spray jets, are produced that travel towards one another at an angle of greater than 0° and equal to or less than 180°, so that the individual aerosol particles at least partially impact with one another and thereby lose kinetic energy. The nozzle openings are preferably arranged so that the linear extensions of the nozzle channels beyond the opening and the longitudinal axis of the nozzle are situated in one plane. In other words, in all the embodiments, the regions of the channels that form the nozzle openings are preferably bent at an angle of greater than 0° and equal to or less than 90° relative to the main longitudinal axis of the valve in question. Angles between 0° and 45° are preferred. An angle of 0° means that the valve opening is aligned with the longitudinal side of the valve.

In a preferred embodiment, the problem on which the invention is based is solved by a nozzle that is a multi-channel nozzle, at least at its head end, the channels of which are inclined at an angle to one another, in the region in front of the nozzle opening as far as the nozzle opening, such that the aerosol jets flowing through them impact with one another downstream behind the nozzle.

The nozzle according to the invention is characterized in that the primary aerosol particles are produced with a high kinetic energy so that the fine particle fraction is correspondingly high. The primary particles are then decelerated again by the jet impaction. The energy released results in some cases in further comminution of these propellant-containing, primary aerosol particles to form secondary aerosol particles.

According to a particularly preferred embodiment, it is envisaged that the nozzle is a two-channel nozzle, both channels of which start at the base region of the valve, i.e., the valve stem, and run through the valve until they are inclined an angle $\alpha$ (see FIG. 1), where $0°<\alpha\leqq180°$, relative to one another in the region of the nozzle openings, so that the respective spray jets or aerosol clouds emerging from the channels travel towards one another. The most suitable angle $\alpha$ is determined depending, inter alia, on the composition of the propellant gas formulation and other parameters.

Preferably, the channels in a multi-channel nozzle have the same diameter and the same length, with the result that the time taken for an aerosol formulation to travel through the nozzle will always be the same, no matter which channel the formulation passes through. This embodiment has the advantage that none of the minimum of two aerosol jets can leave the nozzle prematurely without having an impaction partner.

Other embodiments of this kind have more than two such channels. Preferably, the channels are not directly connected to one another.

In another embodiment, at the base end of the valve, there is only one channel that splits into at least two branches within the valve body, these two branches having the same flow resistance. Preferably, the two branches are of the same length and diameter. Here, too, the two branches move towards each other in the region of the nozzle opening, so that the emergent spray jets or clouds of aerosol move towards one another at an angle $\alpha$ where $0°<\alpha\leqq180°$.

Other embodiments of this kind comprise more than two such channels at the head end in the branching area.

In another embodiment, the problem underlying the invention is solved by the fact that the aerosol container does not contain just one valve, but contains at least two valves. In the minimum of two valves, the channels are angled in the region in front of the openings up to the openings of the nozzles, such that the emergent spray jets or clouds of aerosol move towards one another at an angle $\alpha$, where $0°<\alpha\leqq180°$.

In a preferred variant of this embodiment, the minimum of two valves may be joined together by a means such that the minimum of two valves can only be moved jointly in the vertical direction inside the container, and, as a result, the valves are always opened simultaneously. Such means comprise, for example, a bridge-like rigid bridge that is fixedly attached to both valves, or a common cap that covers the head end of both valves.

A cap has one or more openings above the respective nozzle openings of the individual valves.

A bridge may connect the two valves both at the head end and at the base end, i.e., on the side located outwardly relative to the container or on the side located inwardly relative to the container.

FIG. 1 diagrammatically shows a multi-channel nozzle 1 in the form of a two channel nozzle with two channels 2 and 3. This multi-channel nozzle may be constructed as a spray head in the head region of a valve. The channels 2 and 3 are inclined to one another at an angle $\alpha$. To illustrate the angle, the virtual longitudinal axes, $Lo_1$ and $Lo_2$, respectively, of each valve opening of each channel is shown, the point of intersection of which corresponds to the point of impaction of the aerosol jets/clouds. The point of impaction is generally indicated by the two curved arrows, and angle $\alpha$ is indicated by the curve connecting the two longitudinal axes of each valve opening of channels 2 and 3. The angle $\alpha$ may be greater than 0° and equal to or less than 180°. The inclination not only ensures that an aerosol jet or cloud leaving the channel 2 impacts with an aerosol jet or cloud leaving the channel 3, but also ensures that the aerosol particles slow one another down. In the embodiment shown in FIG. 1, the two channels 2 and 3 are uniformly supplied with the propellant gas formulation.

As already mentioned, the aerosol jets may strike one another at any desired angle between 0° to 180°, at any desired spacing from the surface of the nozzle opening, and at any desired speed. The ratio of the parameters determines the degree of dispersion and the speed of the secondary aerosol cloud formed.

Figure 2:
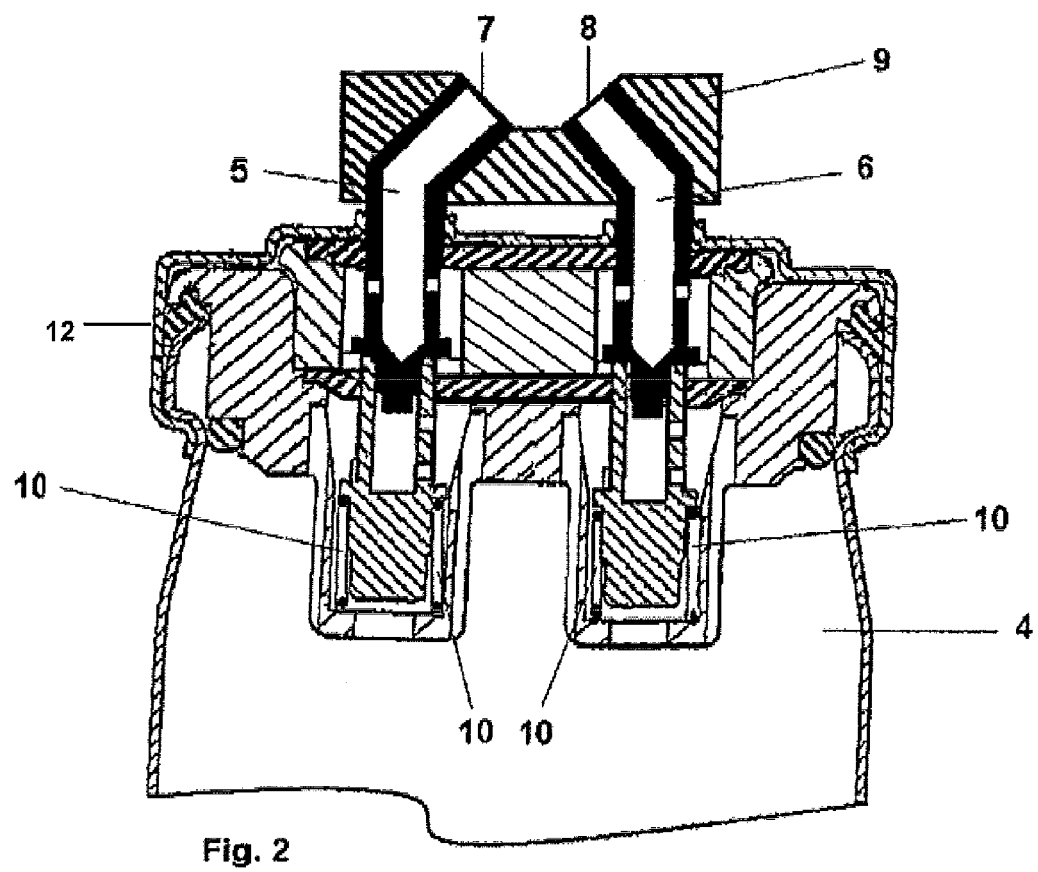
FIG. 2 shows a metering aerosol container according to the present invention comprising a bridged valve system, i.e., two valves fitted with a common cap.

FIG. 2 shows an embodiment of a metering aerosol container 4 with two valves 5 and 6, the openings 7 and 8 of which are inclined relative to one another according to the invention. The two valves 5 and 6 are fitted with a common cap 9 that has at least one opening in front of the valve openings 7 and 8, so that the two valves 5 and 6 can only be moved jointly. The valves may be moved perpendicularly into the container counter to the springs 10. The drawings show the two valve stems, such that they extend parallel to the longitudinal axis of the container (perpendicularly from top to bottom) from their base end to just above valve cup 12 and then bend towards one another above the valve cup 12. In other embodiments, the valve stem is straight and only the channels 7 and 8 leading to the openings are correspondingly angled.

Figure 3:
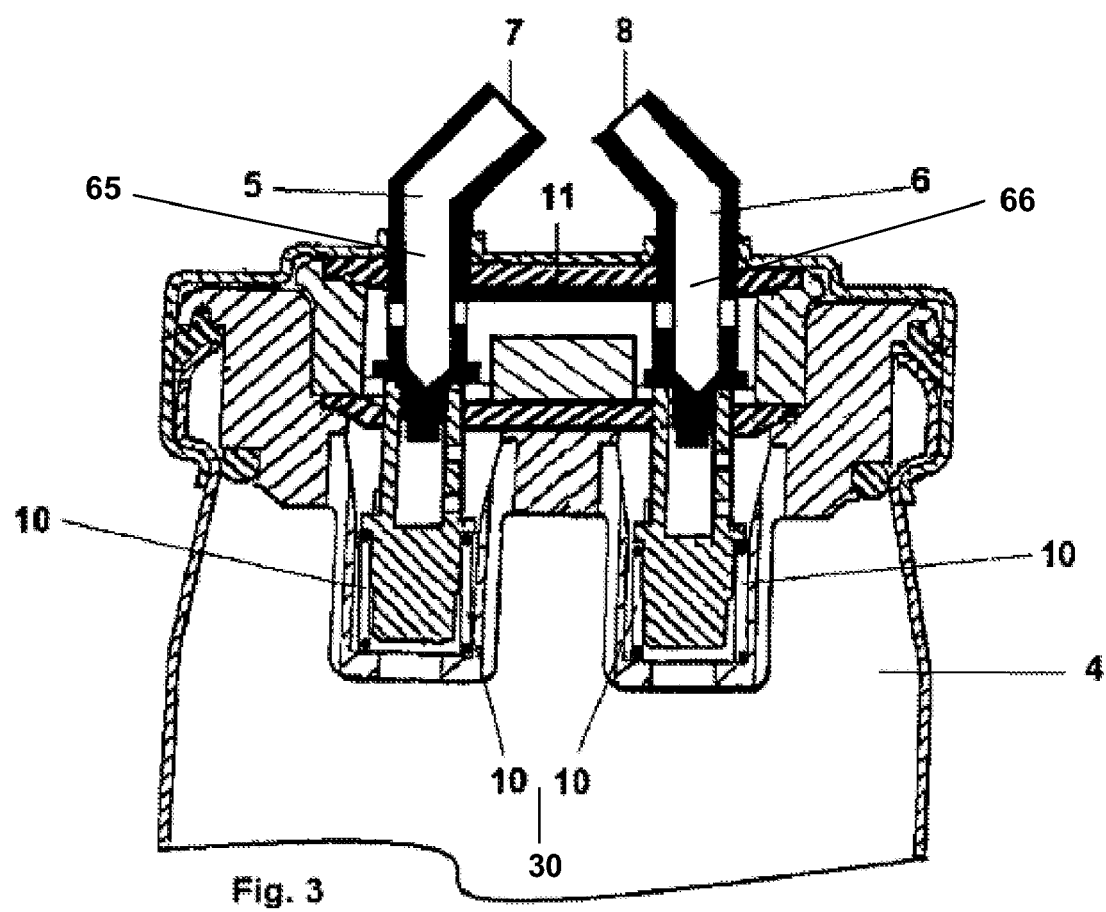
FIG. 3 shows a metering aerosol container according to the present invention comprising a bridged valve system, i.e., two valves fitted with a common bridge.

FIG. 3 shows an embodiment of a metering aerosol container 4 with an interior chamber 30 fitted with two valves 5 and 6. Each of the valves 5, 6 comprises at least one channel 65 and 66 respectively with corresponding openings 7 and 8. The channels 65 and 66 are inclined relative to one another according to the invention. The two valves 5 and 6 are fitted with a common bridge 11 that joins the two valves firmly and rigidly together so that the two valves 5 and 6 can only be moved jointly. With regard to the external shape of the valve, it is also true of this embodiment that the channels 65, 66 do not necessarily have to be bent above the valve cup, but it is possible for only the channels 65, 66 to be bent inside the valve cup (see the description relating to FIG. 2).

Figure 4:
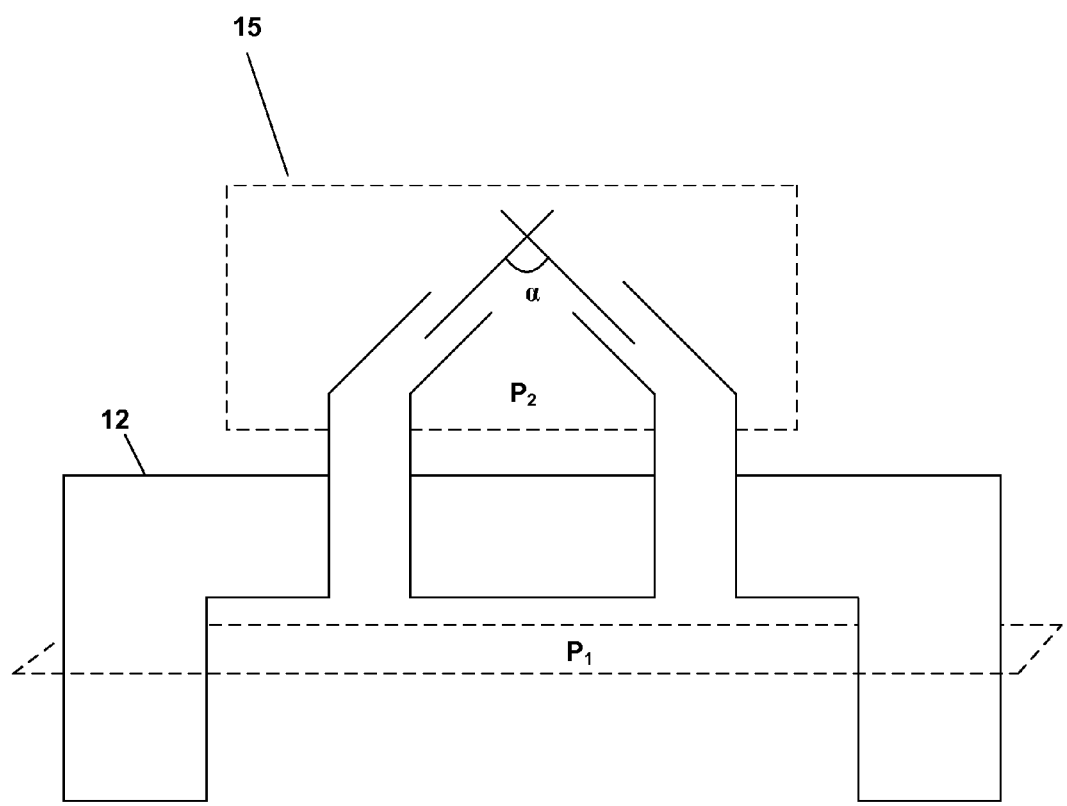
FIG. 4 shows a valve system according to an aspect of the present invention.
Figure 5:
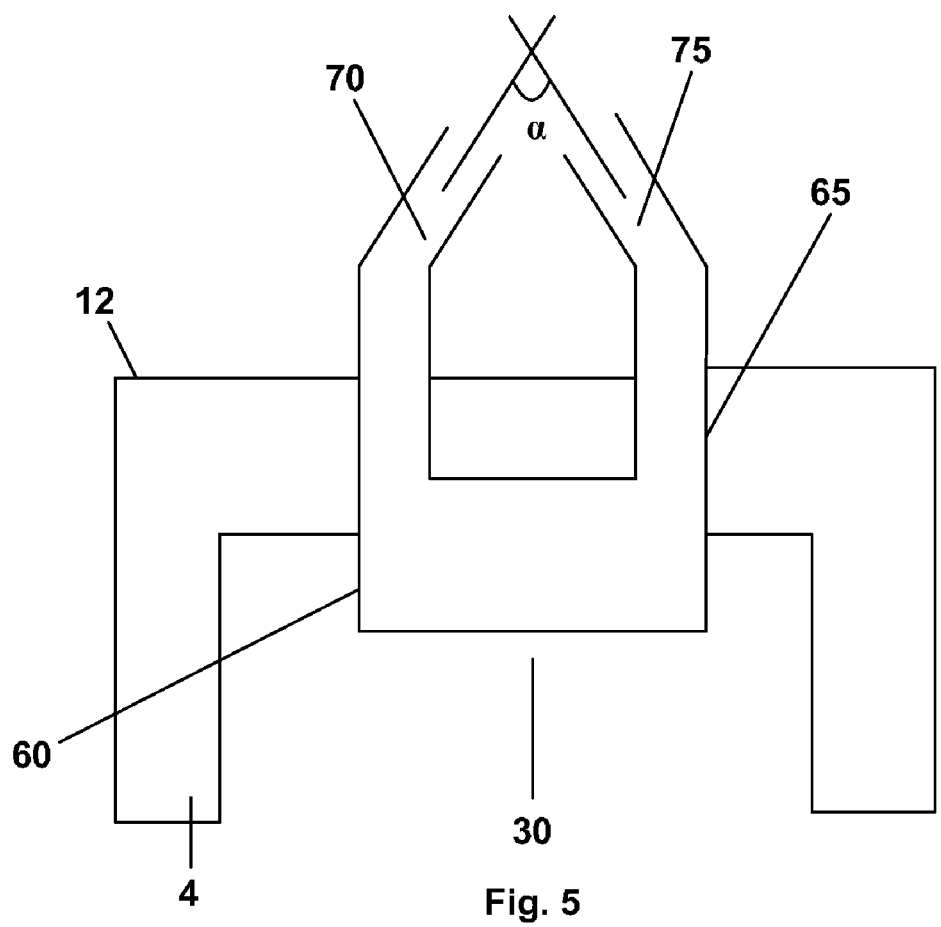
FIG. 5 shows a valve system according to an aspect of the present invention.

FIG. 4 shows a valve system 15 operable to be attached to a metering aerosol container 4 comprising the valve cup 12 substantially defining a first plane $P_1$, and wherein the longitudinal axes of the valve openings 7, 8 extend along a second plane $P_2$ substantially perpendicular to the first plane $P_1$.

FIG. 5 shows a valve system according to an aspect of the present invention. A container 4 with an interior chamber 30 has a valve 20 with a channel 65 that splits into two branches 70, 75 within the valve body 60.

I claim:

1. A valve system for a canister that is operable to dispense at least one dose of propellant-driven pharmaceutical aerosols, the valve system comprising:

a propellant gas pharmaceutical formulation loaded in the canister, the canister comprises an interior chamber;

at least two channels for outwardly conveying the propellant gas pharmaceutical formulation loaded in the canister; at least two valves each comprising at least one of the channels such that the channels extend substantially parallel to a longitudinal axis of the canister and are connected to the interior chamber such that the channels receive the propellant gas pharmaceutical formulation from the interior chamber for dispensing through respective valve openings, and wherein each of the channels defines an angled extension beyond an outer surface of a valve cup of the canister, each angled extension having a longitudinal axis, wherein the longitudinal axis of each of the angled extensions makes an angle between 0° to 90° relative to the longitudinal axis of the canister such that longitudinal axes of the valve openings intersect to define an angle $\alpha$, wherein $0° < \alpha \leqq 180°$, and jets emerging from the valve openings are directed towards one another whereby the jets at least partially impact with one another after leaving the valve openings.

2. The valve system according to claim 1, the at least two channels are not directly connected to one another, and wherein each channel terminates in a respective valve opening.

3. The valve system according to claim 2, wherein the at least two channels have the same length and diameter.

4. The valve system according to claim 1, wherein at least one of the channels splits into at least two branches within a body of at least one of the valves, and wherein each of the at least two branches leads to a respective valve opening.

5. The valve system according to claim 4, wherein the at least two branches have the same length and diameter.

6. The valve system according to claim 1, wherein the valve system is adapted to move vertically and counter to a spring.

7. The valve system according to claim 1, wherein the valve cup substantially defines a first plane, and wherein the longitudinal axes of the angled extensions extend along a second plane substantially perpendicular to the first plane.

8. The valve system according to claim 1, wherein the valve cup substantially defines a first plane, and wherein the longitudinal axes of the angled extensions extend along a second plane at an angle to the first plane.

9. The valve system according to claim 1, wherein the valve cup substantially defines a first plane, and wherein the longitudinal axes of the angled extensions extend along a second plane substantially parallel to the first plane.

* * * * *